United States Patent [19]

Growdon et al.

[11] 4,221,784

[45] Sep. 9, 1980

[54] PROCESS AND COMPOSITION FOR TREATING DISORDERS BY ADMINISTERING LECITHIN

[75] Inventors: John H. Growdon, Brookline; Richard J. Wurtman, Waban, both of Mass.

[73] Assignee: Massachusetts Institute of Technology, Cambridge, Mass.

[21] Appl. No.: 27,209

[22] Filed: Apr. 5, 1979

Related U.S. Application Data

[63] Continuation-in-part of Ser. No. 847,967, Nov. 2, 1977.

[51] Int. Cl.$^2$ ............................................ A61K 31/685
[52] U.S. Cl. .................................................... 424/199
[58] Field of Search ......................................... 424/199

[56] References Cited

U.S. PATENT DOCUMENTS

| 2,064,727 | 12/1936 | Buer | 424/199 X |
|---|---|---|---|
| 3,088,871 | 5/1963 | Pfeiffer | 424/199 X |

FOREIGN PATENT DOCUMENTS 2004409  1/1970  Fed. Rep. of Germany ........... 424/199

Primary Examiner—Stanley J. Friedman
Attorney, Agent, or Firm—Arthur A. Smith, Jr.; Paul J. Cook

[57] ABSTRACT

Lecithin without a drug is administered to a patient in order to increase acetylcholine levels in the brain or other tissues, thereby to alleviate the effects of tardive dykinesia, manic-depressive disease, memory impairment or familial ataxias.

2 Claims, No Drawings

PROCESS AND COMPOSITION FOR TREATING DISORDERS BY ADMINISTERING LECITHIN

The government has rights in this invention pursuant to Grant No. MH-28783 from the National Institute of Mental Health.

REFERENCES TO RELATED APPLICATIONS

This application is a continuation-in-part of Ser. No. 847,967, filed Nov. 2, 1977.

BACKGROUND OF THE INVENTION

This invention relates to a process for the administration of lecithin in the absence of a drug in order to treat human disorders by increasing acetylcholine levels in brain and other tissues.

There are a number of diseases which affect acetylcholine-containing neurons in the brain or other tissues, and which are treated by drugs that cause undesired side effects by diminishing acetylcholine's release; there also exists diseases now treated by other drugs in which the potency and/or efficacy of the drugs could be improved by combining them with choline or natural or synthetic compounds that dissociate to form choline in order thereby to enhance the release of acetylcholine. Such diseases include both those primarily involving the brain (e.g., diseases of higher cortical functions; psychiatric illnesses; movement disorders) and those involving the peripheral nervous system (e.g., neuromuscular disorders). Tardive dyskinesia is a particularly common movement disorder associated with inadequate release of brain acetylcholine as a result of drug administrations for the initial brain disease (e.g., psychosis). Tardive dyskinesia is a choreic movement disorder characterized by involuntary twitches in the tongue, lips, jaw and extremities. It typically occurs in susceptible persons after chronic ingestion of neuroleptic drugs and may involve an imbalance in the postulated reciprocal relation between dopaminergic and cholinergic neurons in the basal ganglions. Thus, drugs that either block catecholamine synthesis (e.g., alpha-methyl-p-tyrosines), deplete the brain of monoamines (e.g., reserpine, tetrabenazine) or antagonize dopamine's actions on synaptic receptors (e.g., pherothiazines, galoperidol) often suppress tardive dyskinesia, whereas drugs that indirectly stimulate dopamine receptors (e.g., amphetamine, levodopa) often exacerbate the abnormal movements. Drugs assumed to increase the amount of acetylcholine within brain synapses (e.g., physostigimine, deanol), also tend to suppress the chorea of tardive dyskinesia, whereas anticholinergics (e.g., scopolamine), make it worse.

We have shown that choline administered by injection or by dietary supplementation increases blood choline levels in the rat; this, in turn, increases choline levels in cholinergic neurons within the brain and elsewhere in the body, thereby accelerating the synthesis of acetylcholine, increasing tissue acetylcholine levels, and increasing the amounts of acetylcholine released into brain synapses. In human beings, oral doses of choline or of lecithin, a naturally-occurring compound that dissociates to choline were found to cause dose-related increases in blood choline levels of sufficient magnitude (based on the studies on rats) to enhance brain acetylcholine synthesis and release; choline levels in the cerebrospinal fluid also rose in parallel. It has also been reported in four human patients that the administration of choline decreased the choreiform movements of tardive dyskinesia; no data were provided as to whether or not the drug given concurrently for psychosis (haloperidol, 3 mg per day) continued to be effective during the brief period of choline administration, and it was concluded that the apparent effectiveness of choline had to be interpreted with caution, since " . . . all four patients with tardive dyskinesia could have been gradually improving during the study" since this disease is characterized by extreme variability of clinical course. Thus, prior to our invention, disclosed in Ser. No. 847,967, filed Nov. 2, 1977, it had not been known that the concomitant administration of choline or of a natural or synthetic compound that dissociates to form choline along with an anti-psychotic drug that causes tardive dyskinesia as a side effect could significantly reduce or prevent the onset of tardive dyskinesia, without blocking the effectiveness of the drug in treating psychosis.

It would be desirable to eliminate the use of drugs in certain patients being treated for psychiatric disease, memory impairment or other brain dysfunctions in order to eliminate undesirable side effects of the drugs. Furthermore, it would be desirable to replace choline as an oral source of precursor for brain acetylcholine since the administration of choline is accompanied by undesirable odor.

SUMMARY OF THE INVENTION

This invention is based upon the discovery that lecithin, when administered alone, optimizes physiological functions and restores impaired physiological functions in situations associated with inadequate cholinergic transmission such as tardive dyskinesia, manic-depressive states or other psychiatric diseases, memory impairment, familial ataxias or the like. The lecithin can be administered orally such as in tablet, capsule, granules or liquid form or parenterally by intravenous, intramuscular or subcutaneous injection.

DETAILED DESCRIPTION OF SPECIFIC EMBODIMENTS

In accordance with this invention, lecithin is administered to a patient without a drug in order to increase blood levels of choline, and thereby to increase the level of acetylcholine in the brain. The acetylcholine is synthesized from choline and acetyl CoA in a reaction catalyzed by choline acetyltransterase (CAT). It has been found that the administration of lecithin alone is useful for the treatment of physiological functions associated with inadequate cholinergic transmission.

There are a number of brain and peripheral diseases involving cholinergic neurons that are presently treated with drugs that are only sometimes effective, or that require very large doses of the drugs (with correspondingly greater cost and incidence of side effects); some of these diseases can be effectively treated by replacing the existing drug therapy with the administration of lecithin. One example is the mania phases of manic-depressive psychosis, which is currently treated with lithium salts. These salts, as a side effect, can cause toxic changes in the kidneys. The administration of lecithin would allow for effective treatment of the mania without the lithium dose. Another example is memory impairment occurring in apparently normal people or those associated with aging or with neurological diseases. There is no adequate current mode of treatment. In addition, lecithin alone may be used to treat patients with familial ataxia, another degenerative disease for which there is no adequate treatment.

The lecithin can be administered as lecithin with either saturated or unsaturated fatty acid side chains. The lecithin is administered so that a choline level of at least about 10-25 nanomoles/ml and usually between about 10 and 50 n moles/ml is attained in the patient's blood stream. When utilizing lecithin in a liquid carrier, it is administered in amounts of between about 0.1 and 100 g/day. When lecithin is administered in granular form, as a tablet or in a capsule, it is employed in amounts of between about 0.1 and 100 g/day, usually between about 30 and 50 g/day. Normally, lecithin is not available as a pure compound and is available in admixture with other phospholipids wherein the lecithin comprises about 20-30 weight percent of the mixture.

The following example illustrates the present invention and is not intended to limit the same.

EXAMPLE I

This example illustrates that lecithin significantly improves memory loss in a normal patient.

A patient who was not taking medication, but who had suffered memory loss, but who did not suffer from any other brain dysfunction or from any psychiatric disease was treated with lecithin. Prior to the lecithin treatment, he was tested for memory quotient and intelligence quotient by the Wechsler Memory & Intelligence tests; his memory quotient was 122.

Lecithin obtained from the Nattermann Corporation and which comprises 80% lecithin was orally administered to the subject at a dosage of 10 g. every 8 hours over a period of 6 weeks. The dosages were prepared by mixing the lecithin in foods.

Blood samples for choline measurements were collected from the subject before the lecithin trial began and 6 weeks later during lecithin ingestion; plasma samples were separated, frozen and assayed for choline content by a conventional radioenzymatic method.

Before treatment, plasma choline levels were 12. g$\pm$1.1 nmol per milliliter. After lecithin ingestion, plasma choline levels in blood obtained 4 hours after a lecithin dose increased to 30.3$\pm$2.7 nmol per milliliter ($P<0.01$). During the 6th week of lecithin ingestion at a time the plasma choline level was significantly elevated, his memory quotient improved to 140.

We claim:

1. The process of improving memory impairment associated with inadequate cholinergic transmission in a human afflicted with memory impairment which comprises administering to the human an amount of lecithin effective to release adequate amounts of brain acetylcholine to improve said memory impairment.

2. The process of claim 1 wherein the lecithin is administered orally.

* * * * *